(12) United States Patent
Lombardi

(10) Patent No.: US 9,000,105 B2
(45) Date of Patent: Apr. 7, 2015

(54) ANTIPATHOGENIC GUANIDINIUM COPOLYMER

(71) Applicant: John L. Lombardi, Tucson, AZ (US)

(72) Inventor: John L. Lombardi, Tucson, AZ (US)

( * ) Notice: Subject to any disclaimer, the term of this patent is extended or adjusted under 35 U.S.C. 154(b) by 135 days.

(21) Appl. No.: 13/839,075

(22) Filed: Mar. 15, 2013

(65) Prior Publication Data

US 2014/0275447 A1    Sep. 18, 2014

(51) Int. Cl.
*A01N 47/44* (2006.01)
*A01N 55/00* (2006.01)

(52) U.S. Cl.
CPC .............. *A01N 47/44* (2013.01); *A01N 55/00* (2013.01)

(58) Field of Classification Search
CPC ................................ A01N 47/44; C08G 73/02

USPC .......................................................... 525/540
See application file for complete search history.

(56) References Cited

U.S. PATENT DOCUMENTS

| 4,675,134 | A | * | 6/1987 | Miura et al. ..................... 562/86 |
| 4,945,112 | A | * | 7/1990 | Zipplies et al. ............... 514/555 |
| 5,728,734 | A | * | 3/1998 | Sato .............................. 514/555 |
| 5,962,518 | A | * | 10/1999 | Stenzel et al. ................ 514/491 |
| 6,673,890 | B1 | * | 1/2004 | Boeckh et al. ................ 528/229 |
| 2009/0032057 | A1 | * | 2/2009 | McCormick et al. ............. 134/3 |
| 2011/0269936 | A1 | * | 11/2011 | Tets et al. ...................... 528/422 |

* cited by examiner

*Primary Examiner* — Mike M Dollinger
(74) *Attorney, Agent, or Firm* — Dale F. Regelman; Quarles & Brady LLP

(57) ABSTRACT

Antimicrobial, substituted alkyl guanidinium polymers, and methods to form same.

7 Claims, 19 Drawing Sheets

520

730

ANTIPATHOGENIC GUANIDINIUM COPOLYMER

TECHNICAL FIELD

Applicant's invention relates to a guanidinium polymer that is effective as a broad-spectrum disinfectant capable of immobilizing and/or killing pathogens, including active bacteria and dormant bacteria spores.

BACKGROUND ART

The presence of certain types of bacteria and other pathogens, whether airborne or on exposed surfaces, creates a health risk. These pathogens may be naturally occurring in the environment or may be introduced by a sick or infected personal or animal. The risk of harm from pathogens is particularly a concern in healthcare settings, such a hospitals and nursing homes, where individuals are more likely to have weakened immune systems. Certain pathogens may be "weaponized," and used as biological agents against both civilian and military personnel. These include anthrax (*Bacillus anthracis*) and botulinum (*Clostridium botulinum*).

To minimize the risk of harm as a result of exposure to bacteria, it has been a goal to develop substances and/or treatments that are effective in reducing or eliminating harmful bacteria. For instance, disinfectants are commonly applied to surfaces (i.e., floors, walls, work surfaces, and the like) to reduce or eliminate any exposed bacteria. These disinfectants, however, generally reside only on the surface and are, as such, easily washed away or otherwise removed. Such disinfectants must be periodically reapplied to maintain their effectiveness.

Bacteria exist in either an active or a dormant state. In the active state, often referred to as the "vegetative state," the bacteria is capable of growing and reproducing. It is in this state that the bacteria causes infections and illnesses. In the dormant state, often referred to as "spores," "endospores" or "microbial cysts," the bacteria is surrounded by a very tough outer coating. A bacteria spore requires little or no nutrients, can survive for a long period of time in harsh conditions, and is resistant to ultraviolet radiation, high and low temperature extremes, desiccation, and most chemical disinfectants. As such, disinfectants may be highly effective against bacteria in the vegetative state, but generally have little or no effect on the same bacteria in the dormant state. Strong oxidants, such as peroxyacetic acid, are capable of killing spores, but have the disadvantages of a limited shelf life, an unpleasant odor, and causing irritation to the skin, eyes, and respiratory system upon exposure.

Accordingly, it would be an advance in the state of the art to provide an antipathogenic composition that is (i) capable of effectively killing bacteria in the vegetative state, (ii) capable of effectively killing bacteria in the dormant state, (iii) capable of retaining its antipathogenic properties over a long period of time, (iv) capable of coating hard or soft surfaces to form an antipathogenic surface, (v) effective in relatively small concentrations, and (vi) capable of receiving various functional compounds to enhance the efficacy against vegetative and dormant bacteria and non-bacterial pathogens.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

Referring to the foregoing paragraphs, this invention is described in preferred embodiments in the following description with reference to the Figures, in which like numerals represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the above description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Figure 1:
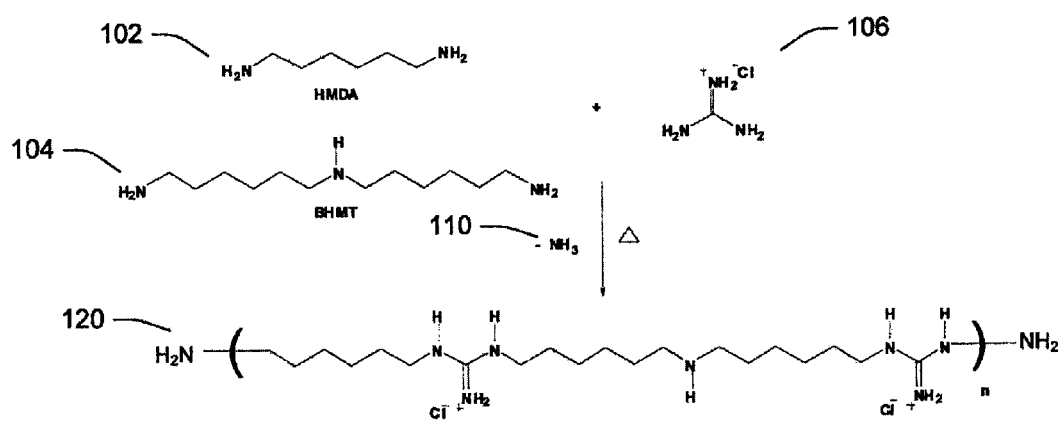
FIG. 1 summarizes the chemical components and reaction used to make Applicant's antipathogenic co-polymer 120.

In certain embodiments Applicant reacts about one equivalent each of hexamethylenediamine (HMDA) 102, bis(hexamethylene)triamine (BHMT) 104, and guanidinium hydrochloride 106 under heat. Ammonia 110 is eliminated as a byproduct of the reaction product. In one embodiment, Applicant's antipathogenic copolymer comprises a structure:

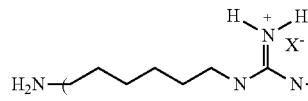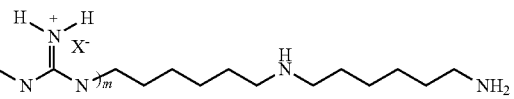

wherein (n) is between 1 and about 100, and wherein m is between 1 and about 100. Referring to FIG. 1, co-polymer 120 comprises a plurality of guanidinium salt moieties.

Figure 2A:
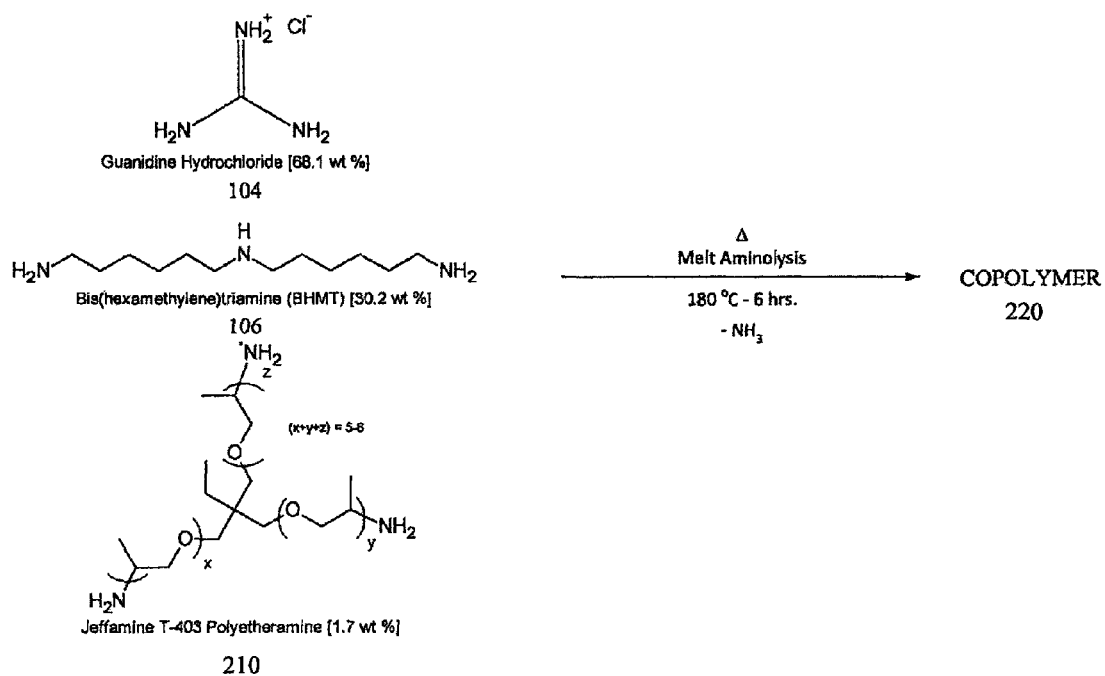
FIG. 2A shows the starting materials used to prepare Applicant's branched antipathogenic guanidinium copolymer 220.

Referring now to FIG. 2A, Applicant has prepared a branched random copolymer 220 by the reaction of guanidine hydrochloride 104, Bis(hexamethylenetriamine) 106, and amino-capped polyether 210. In certain embodiments, amino-capped polyether 210 comprises Jeffamine T-403 sold in commerce by the Huntsman corporation.

Figure 2B:
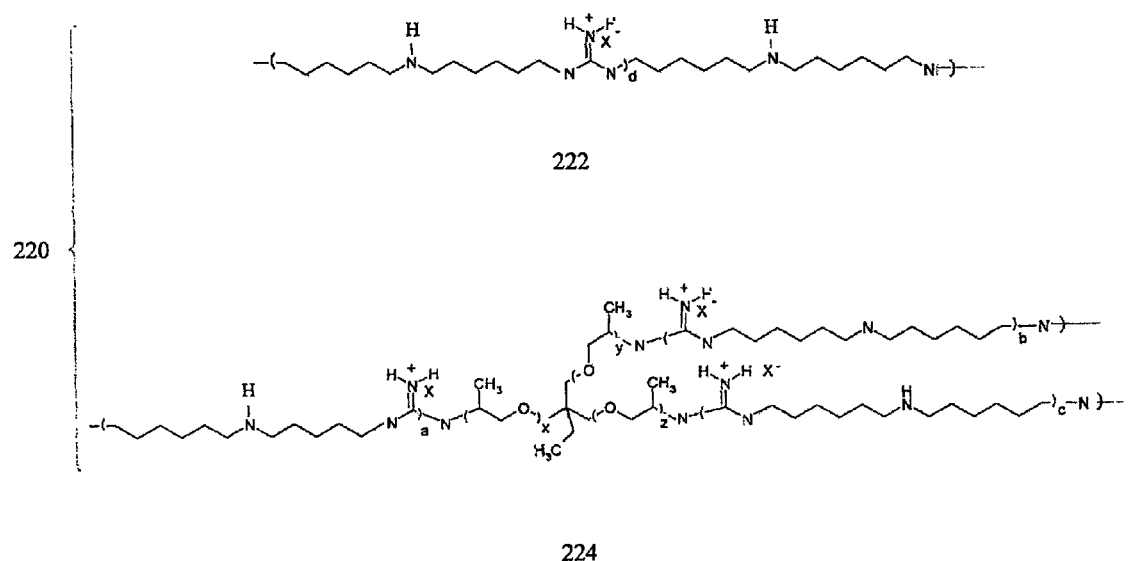
FIG. 2B shows the repeat units comprising Applicant's branched antipathogenic guanidinium copolymer 220.

Referring now to FIG. 2B, in certain embodiments copolymer 220 comprises linear repeat units 222, wherein (d) is between about 10 and about 100, in combination with branching repeat unit 224, wherein (x)+(y)+(z) is between about 3 and about 10, and wherein (a), (b), and (c) are each independently between about 10 and about 100.

The utility of Applicant's antimicrobial alkyl guanidinium polymers can be enhanced by attachment of zwitterionic sulfobetaine groups. Sulfobetaines inhibit protein adsorption to surfaces and hence impart biofouling resistant properties to these already antimicrobial/antipathogenic polymers.

Sulfobetaines are typically prepared via reaction of a tertiary amine with either butane sultone or propane sultone under reflux conditions whereby the sultone ring is opened by the amine. Similarly biofouling resistant zwitterionic carboxybetaine materials can be prepared via substitution of cyclic sultones with either haloacetic acid salts (e.g. chloroacetic or bromoacetic acids) or their esters (e.g. methyl chloroacetate/bromoacetate, ethyl chloroacetate/bromoacetate) under alkaline reaction conditions.

Figure 3A:
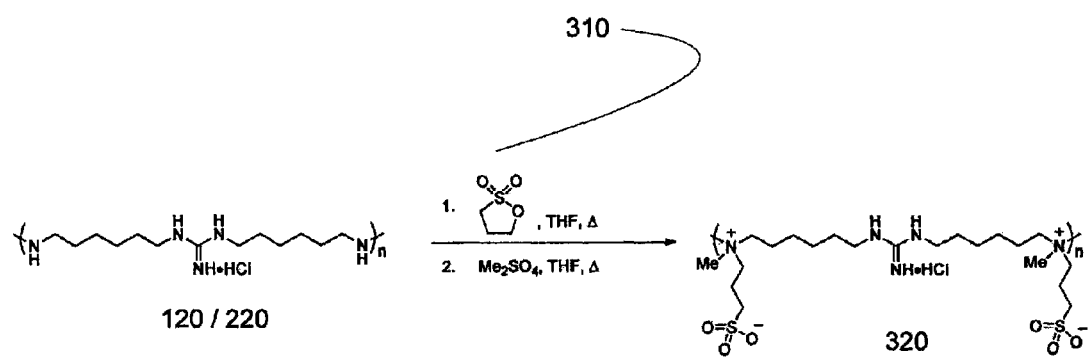
FIG. 3A illustrates alkyl guanidinium polymer 120 or 220 reacted with propane sultone 310 and then dimethyl sulfate to give an alkyl guanidinium polymer.

Referring now to FIG. 3A, alkyl guanidinium polymer 120 or 220 (1 g) was first swelled in warm THF solvent (10 mL, 60° C.) for 2-3 hours. The swollen polymer formed a highly porous globular matter. The flask was then cooled to room temperature, and then propane sultone 310 (0.32 mL) reagent was added to the flask followed by heating at 35-40° C. for 4 hours. Under these conditions, the propane sultone ring was opened upon reaction with the secondary amine groups present along the guanidinium polymer backbone. The flask was cooled to room temperature again and dimethyl sulfate (0.38 mL) was then added followed by warming the flask contents to 50-60° C. for 3-4 hours. Dimethyl Sulfate methylated the tertiary amine groups formed upon the previously sultone grafted polymer backbone producing biofouling resistant zwitterionic repeat units along the alkyl guanidinium polymer 320 backbone. In certain embodiments, n is between about 10 and about 100. In certain embodiments, n is between about 1000 and about 10,000. In certain embodiments, n is between about 10,000 and about 1,000,000.

The solid product was then collected by filtration and sequentially washed with acetone and later ethanol solvents.

Figure 3B:
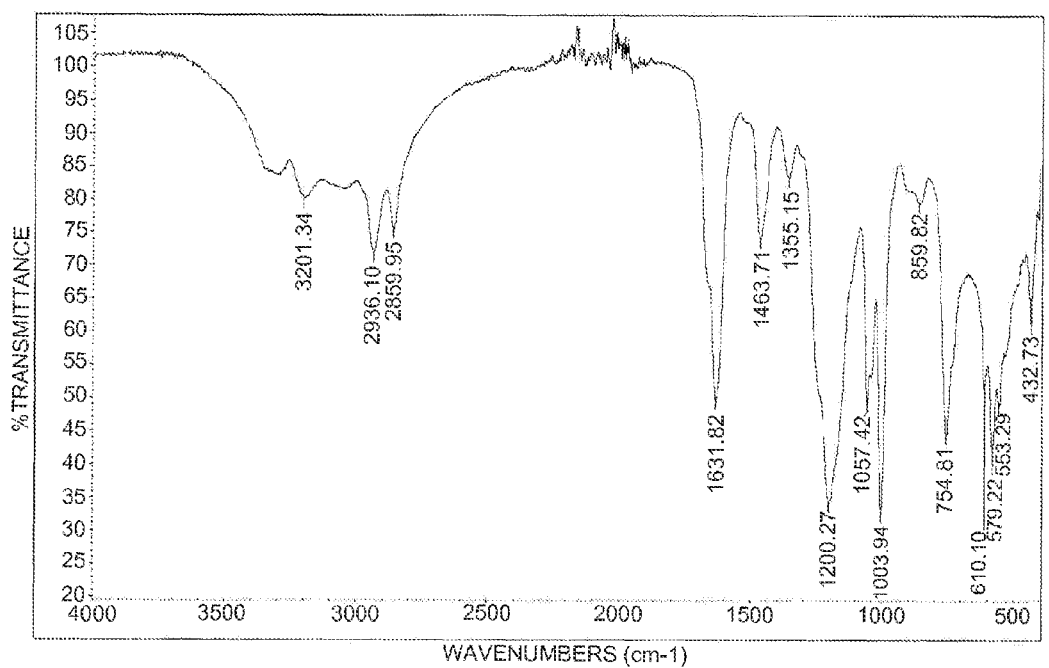
FIG. 3B recites FTIR Spectrum 320 for the alkyl guanidinium polymer of FIG. 3A.

The final product was hygroscopic due to the additional charges it carried, and had the FTIR Spectra 320 shown in FIG. 3B.

Figure 4A:
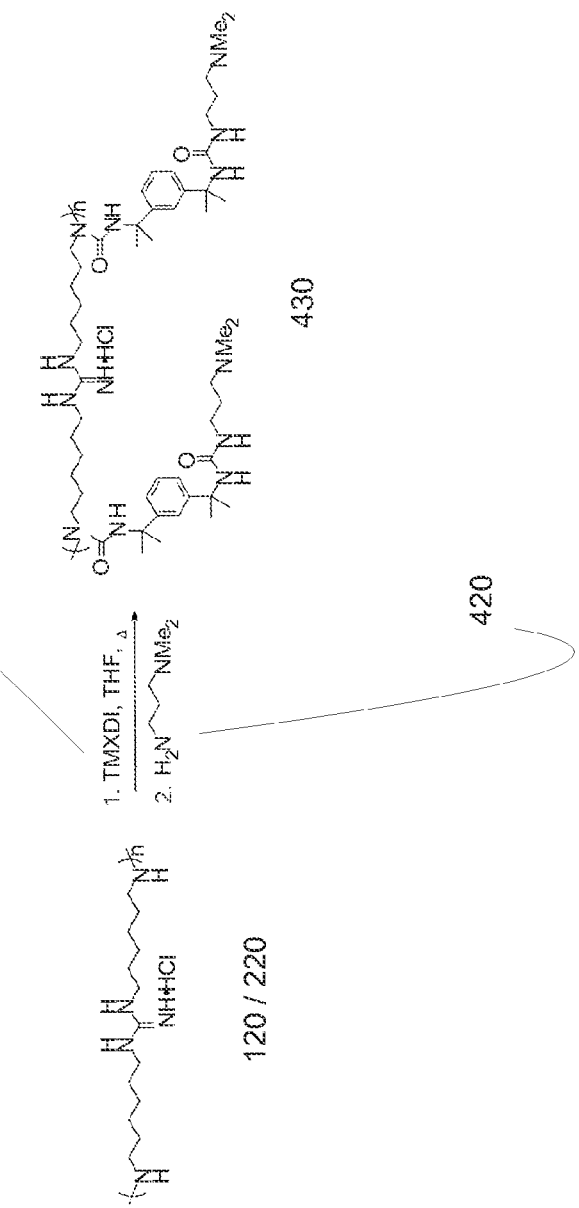
FIG. 4A illustrates a resaction sheme wherein polyalkyl guanidinium polymer 120 or 220 was reacted with meta tetramethylxylylene diisocyanate 410 and then 1,3-diamonopropane 420 to prepare a polymer 430.

Referring now to FIG. 4A, polyalkyl guanidinium polymer 120 or 220 was pre-swelled in warm THF solvent overnight. To the mixture was then added meta tetramethylxylylene diisocyanate 410 (TMXDI—Cytec Industries, Inc. Stamford, Conn.) (450 mg), and the reaction mixture was then heated to reflux for 1 hour. The reaction was subsequently cooled down to 30-40° C. and 1,3-diamonopropane 420 (0.28 mL) reactant was then added to give polymer 430. In certain embodiments, n is between about 10 and about 100. In certain embodiments, n is between about 1000 and about 10,000. In certain embodiments, n is between about 10,000 and about 1,000,000.

Figure 4B:
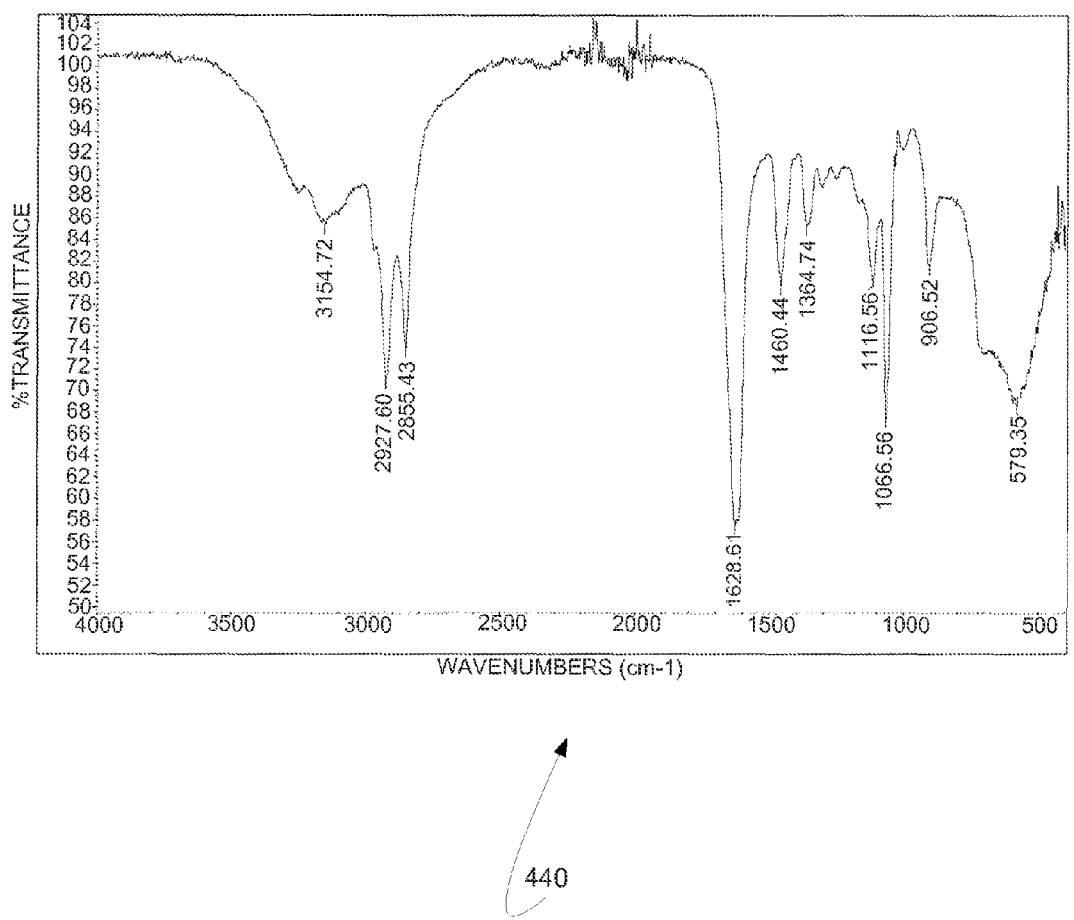
FIG. 4B illustrates FTIR Spectra 440 of polymer 430.

The resultant mixture was maintained at this temperature for 2 hours. The reaction was then filtered and rinsed with acetone. FIG. 4B illustrates FTIR Spectra 440 of the polymer 430.

Figure 5A:
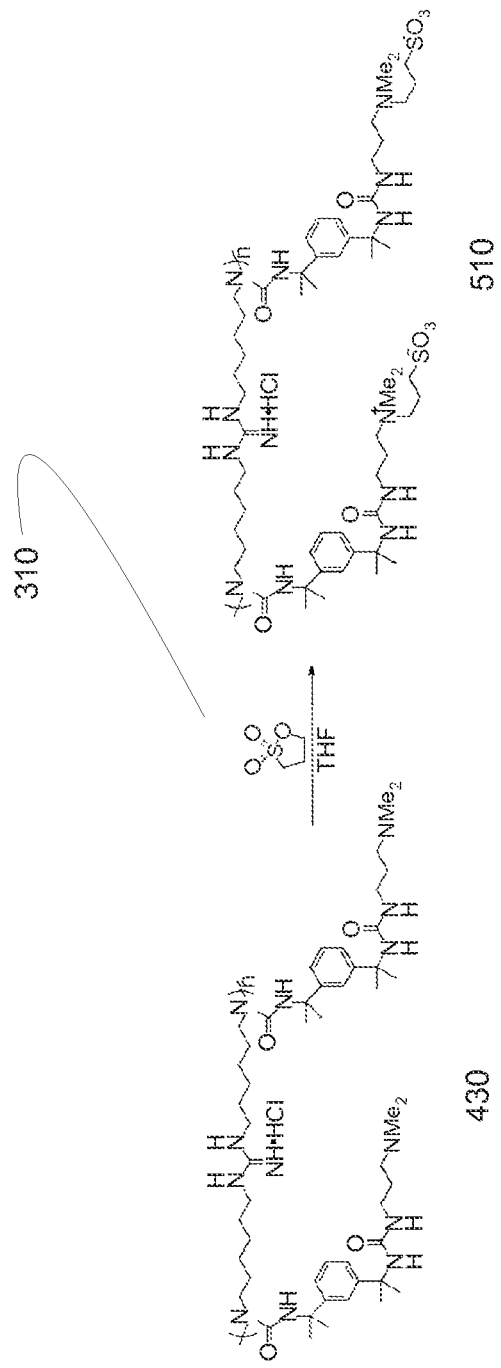
FIG. 5A illustrates copolymer 430 reacted with propane sultone 310 to give sulfobetaine grafted polymer 510.

Referring now to FIG. 5A, copolymer 430 (FIG. 4A) in THF was added propane sultone 310 (0.19 mL). The mixture was stirred at 30-40° C. for 24 hour to give sulfobetaine grafted polymer 510. In certain embodiments, n is between about 10 and about 100. In certain embodiments, n is between about 1000 and about 10,000. In certain embodiments, n is between about 10,000 and about 1,000,000.

Figure 5B:
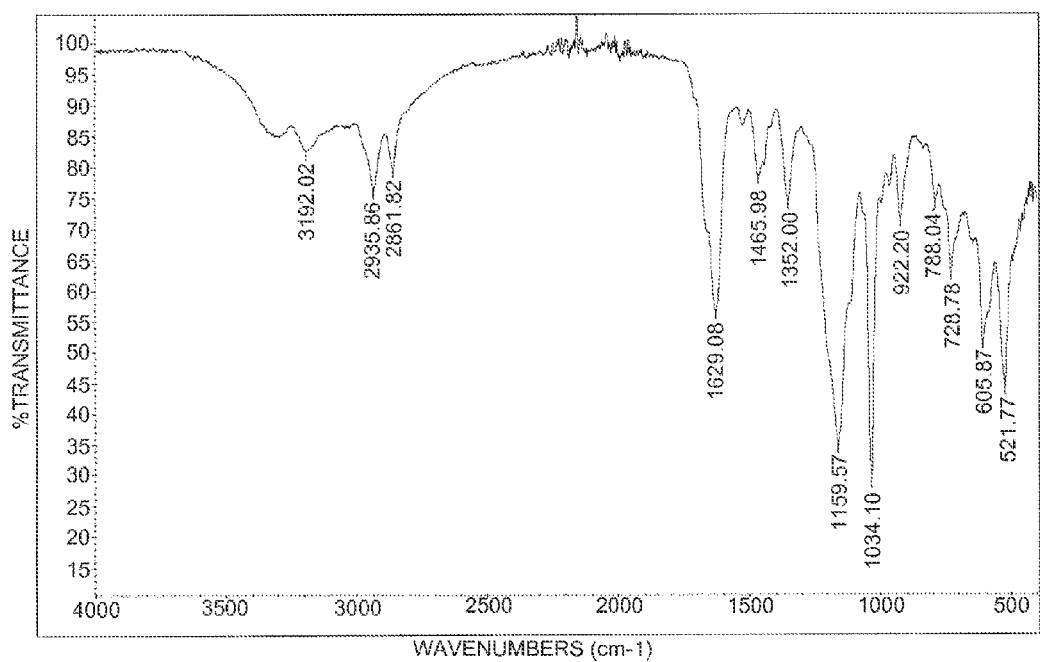
FIG. 5B recites a FTIR Spectra 520 of sulfobetaine grafted polymer 510.

The reaction was then filtered and rinsed with acetone. FIG. 5B recites a FTIR Spectra 520 of sulfobetaine grafted polymer 510.

Figure 6A:
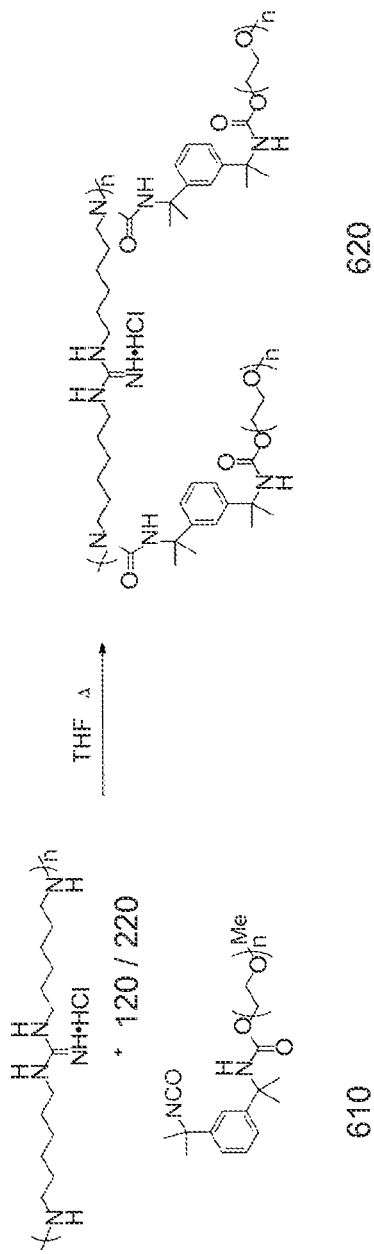
FIG. 6A illustrates reacting polymer 120 or 220 with a mixture of TMXDI 610 and Dow Carbowax Methoxypolyethylene Glycol 550 to give polymer 620.
Figure 6B:
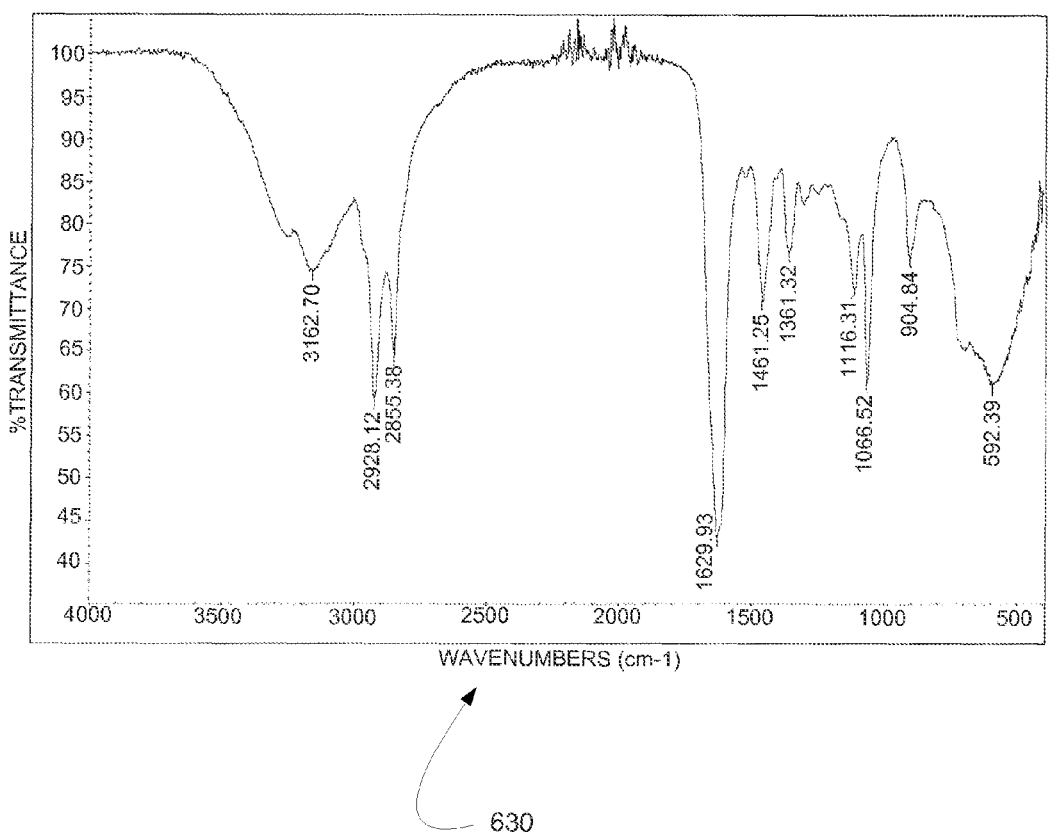
FIG. 6B illustrates FTIR spectrum 630 for polymer 620.

Referring to FIG. 6A, a mixture of TMXDI 610 (450 mg) and Dow Carbowax Methoxypolyethylene Glycol 550 Mn MW (mPEG 550) (1 g) was heated to 100-120° C. The reaction was closely monitored by IR, and ceased until the significant reduction of the O—H stretching signal of mPEG. To the oily adduct was added polymer 120 or 220 (0.5 g) in THF (10 mL). The mixture was heated at 50-60° C. overnight. The reaction was cooled to room temperature, filtered and polymer 620 was washed with acetone and ethanol solvents sequentially. In certain embodiments, n is between about 10 and about 100. In certain embodiments, n is between about 1000 and about 10,000. In certain embodiments, n is between about 10,000 and about 1,000,000. FIG. 6B illustrates FTIR spectrum 630 for polymer 620.

Figure 7A:
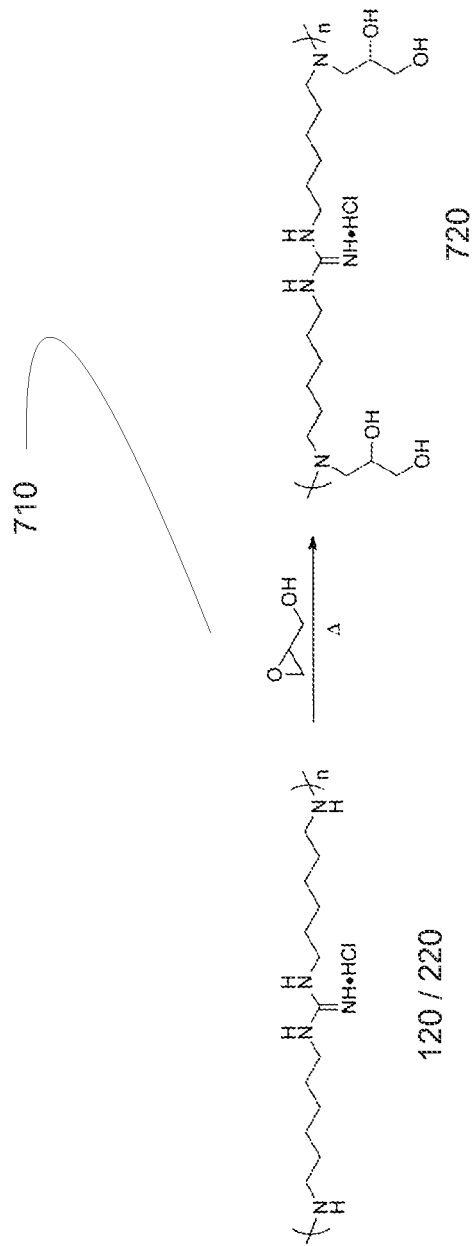
FIG. 7A illustrates glycidol 710 grafted onto the backbone of alkyl guanidinium polymer 120 or 220.

Referring to FIG. 7A, glycidol 710 was grafted onto the backbone of alkyl guanidinium polymer 120 or 220 via ring opening reaction with secondary amine groups. The resultant polymer 720 exhibits greater hygroscopic character as well as has greater tackiness/surface adhesion compared to the unmodified alkyl guanidinium polymer. In certain embodiments, n is between about 10 and about 100. In certain embodiments, n is between about 1000 and about 10,000. In certain embodiments, n is between about 10,000 and about 1,000,000.

An added advantage of glycidol grafting is that the resultant 1,2-diol groups formed upon the polymer backbone can be subsequently crosslinked using inexpensive borates (e.g. boric acid or alkali borates or blends thereof), silicates (e.g. lithium silicate, potassium silicate, tetraalkylammonium silicate or blends thereof), water soluble titanates (e.g. triethanolamine titanate, titanium lactate), or water soluble zirconates (e.g. ammonium zirconium carbonate, potassium zirconium carbonate, triethanolamine zirconate, zirconium lactate). Additionally, glycidol modified alkyl guanidinium polymers can be attached to hydroxylated surfaces (e.g. cellulosic, polyvinyl alcohol, glass, metal oxide surfaces) via chemisorption or via the aforementioned borate, silicate, titanate or zirconate adhesion promoters.

Figure 7B:
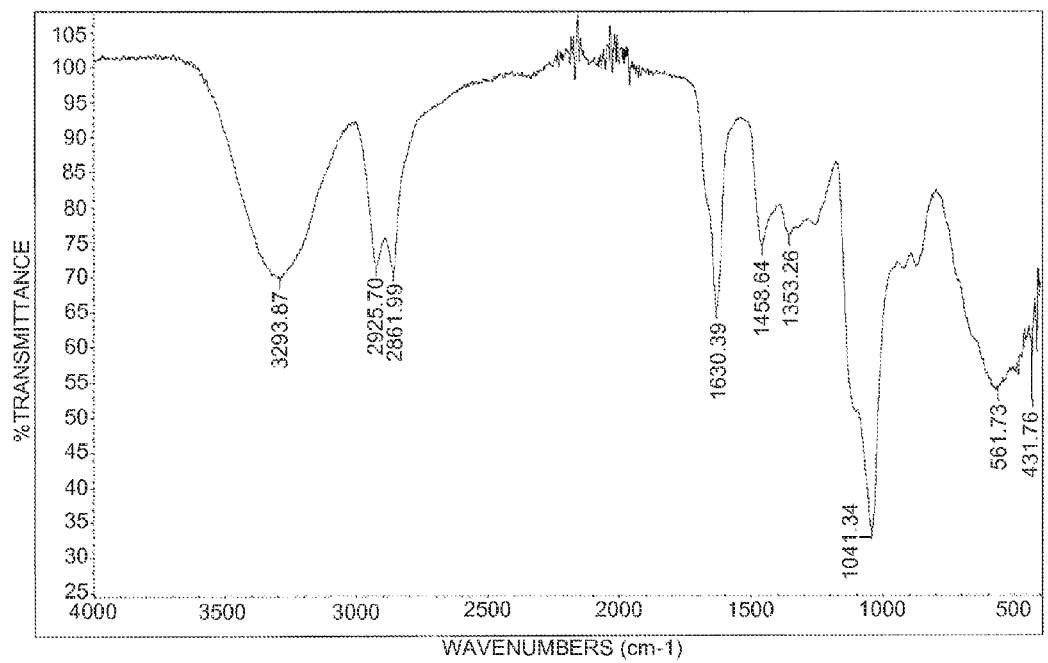
FIG. 7B recites FTIR Spectrum 730 of a glycidol modified polymer 720.

To alkyl guanidinium polymer 120 or 220 (1 g) was added glycidol 710 (3 mL), and the mixture was heated at 50-60° C. for 1 hour. The resultant white/slightly yellow solid polymer 720 had a tacky, mucous like consistency upon cooling and readily adhered upon a wide variety of surfaces including glass, metal and plastics. FIG. 7B recites FTIR Spectrum 730 of the glycidol modified polymer 720.

Figure 8A:
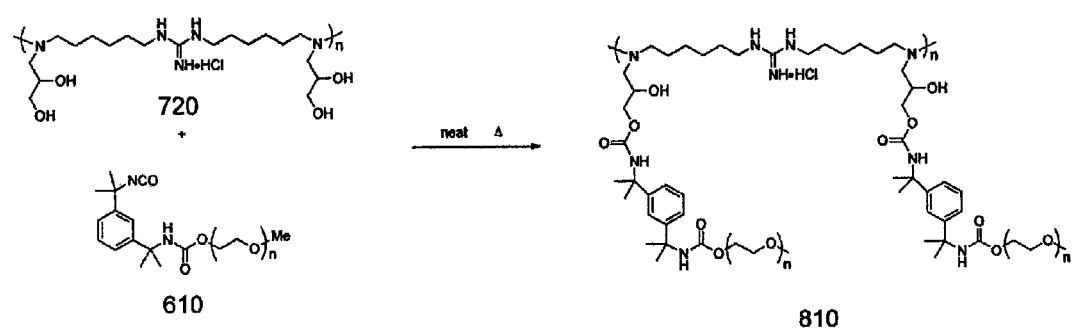
FIG. 8A illustrates glycidolized polymer 720 being reacted with a mixture of TMXDI 610 and mPEG 550 to give polymer 810.
Figure 8B:
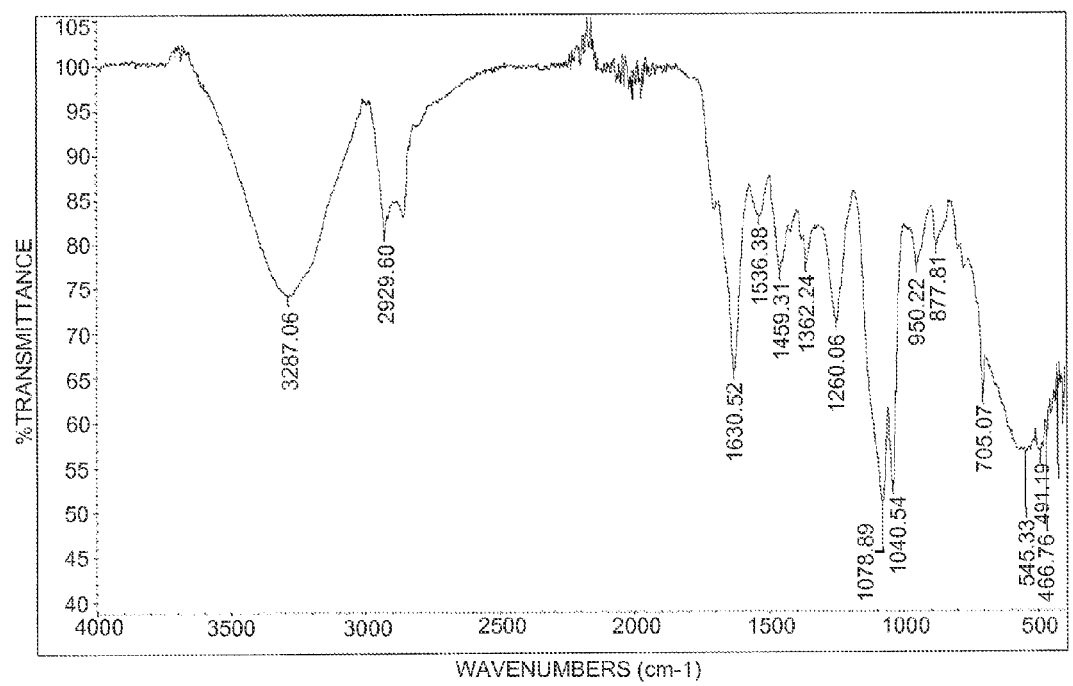
FIG. 8B recites FTIR Spectrum 820 for polymer 810.

Referring to FIG. 8A, a mixture of TMXDI 610 (380 mg) and mPEG 550 (850 mg) was heated to 100-120° C. The reaction was closely monitored by IR, and ceased until the significant reduction of the O—H stretching signal of mPEG. To the oily adduct was added 'glycidolized' polymer 720 (0.5 g). The mixture was heated in neat at 50-60° C. for 2 hours. The reaction was cooled to room temperature, filtered and washed with acetone and ethanol sequentially to give polymer 810. In certain embodiments, n is between about 10 and about 100. In certain embodiments, n is between about 1000 and about 10,000. In certain embodiments, n is between about 10,000 and about 1,000,000. FIG. 8B recites FTIR Spectrum 820 for polymer 810.

Figure 9A:
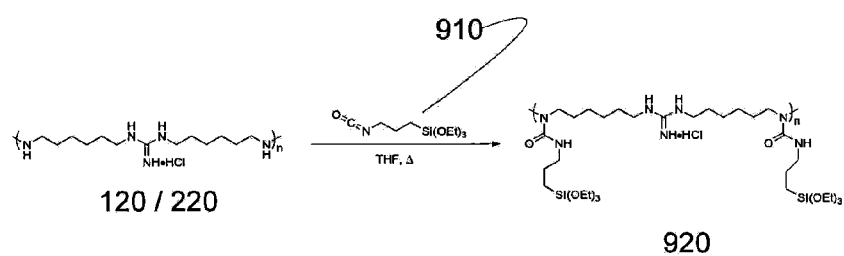
FIG. 9A illustrates alkyl guanidinium polymer 120 or 220 (0.5 g) reacted with isocyanatopropyltriethoxysilane 910 organosilane reactant to form a substituted organosilane grafted urea polymer 920.

Referring now to FIG. 9A, alkyl guanidinium polymer 120 or 220 (0.5 g) was swollen within a flask containing warm THF solvent (10 mL, 60° C.) for 1-2 hours. The flask was then cooled to room temperature and isocyanatopropyltriethoxysilane 910 (0.45 mL) organosilane reactant was then added to the flask followed by heating at 35-40° C. for 2-3 hours. Under these conditions, the isocyanate group on the organosilane reacted with the secondary amine groups present along the alkyl guanidinium polymer backbone and formed a substituted organosilane grafted urea polymer 920. In certain embodiments, n is between about 10 and about 100. In certain embodiments, n is between about 1000 and about 10,000. In certain embodiments, n is between about 10,000 and about 1,000,000.

Figure 9B:
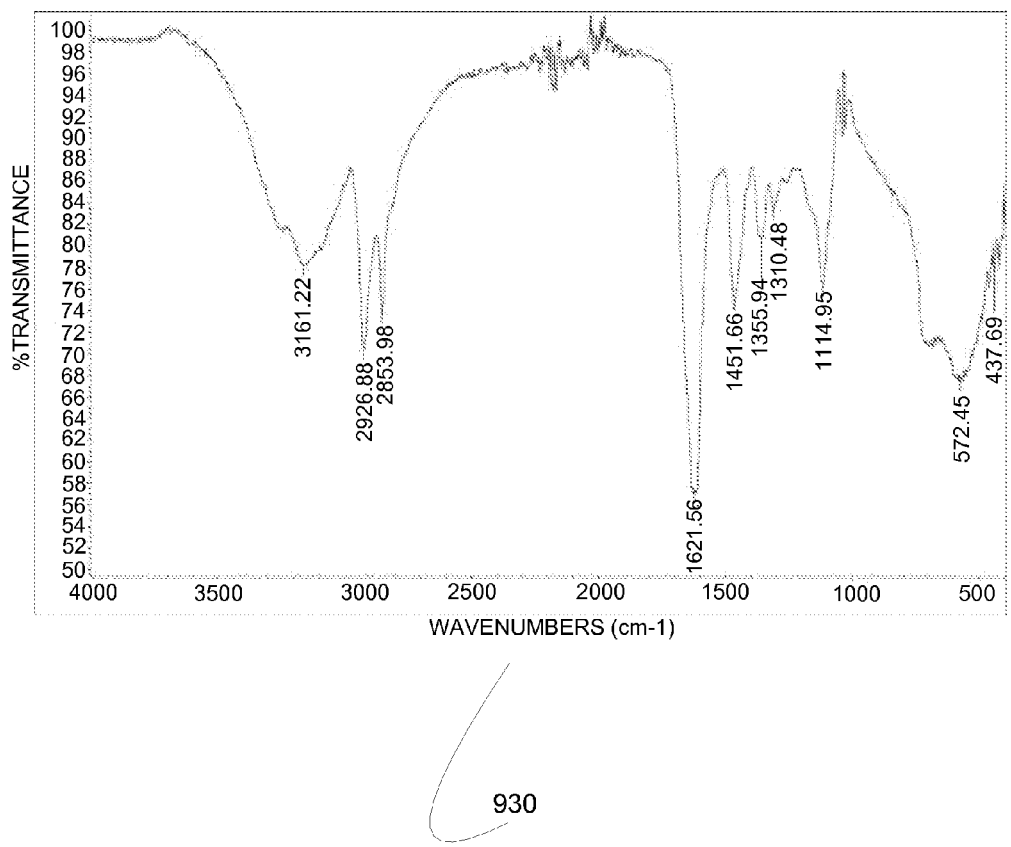
FIG. 9B recites FTIR Spectrum 930 for polymer 120/220.
Figure 9C:
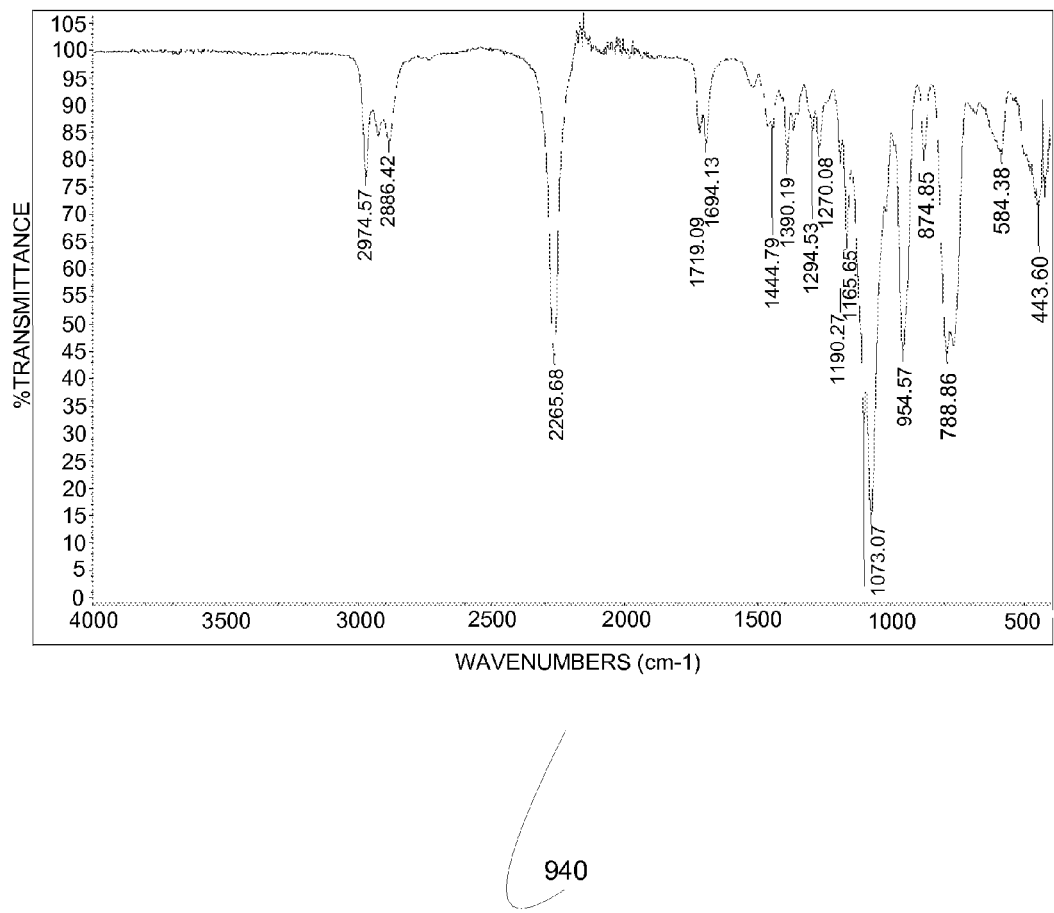
FIG. 9C recites FTIR Spectrum 940 for Isocyanatopropyltriethoxysilane 910.
Figure 9D:
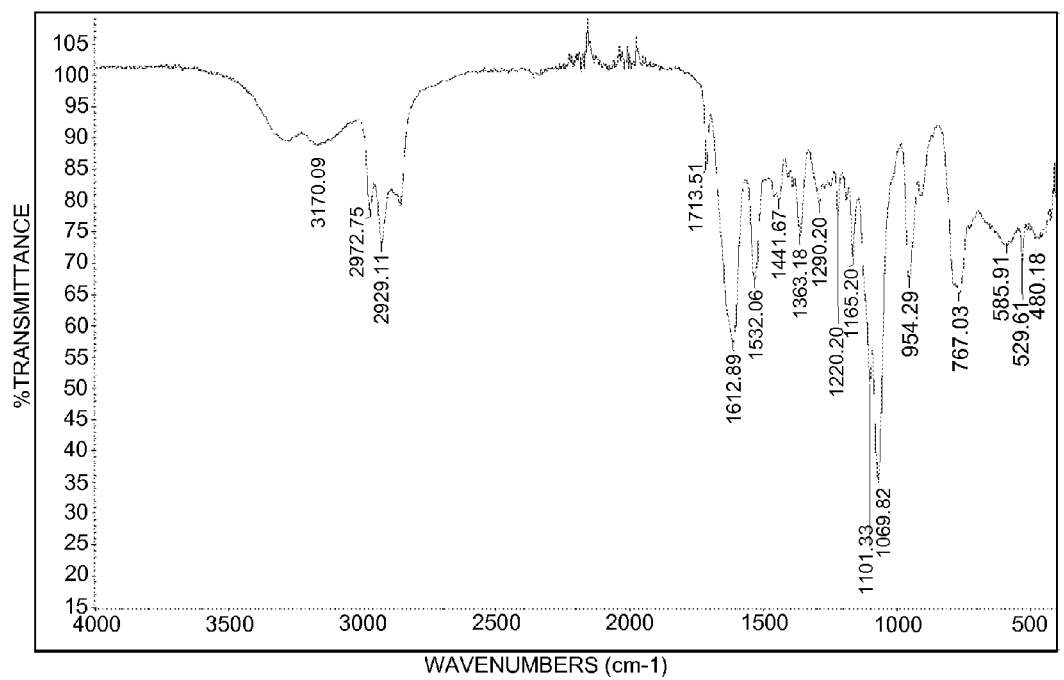
FIG. 9D recites FTIR Spectrum 950 for organosilane grafted urea polymer 920.

FIG. 9B recites FTIR Spectrum 930 for polymer 120/220. FIG. 9C recites FTIR Spectrum 940 for Isocyanatopropyltriethoxysilane 910. FIG. 9D recites FTIR Spectrum 950 for organosilane grafted urea polymer 920.

This organosilane grafted polymer product could be subsequently be coated and adhered upon a wide variety of surfaces via inter and intramolecular sol gel promoted hydrolysis—condensation crosslinking reactions.

The solid organosilane grafted product was then collected by filtration and sequentially washed by acetone and ethanol. As can be seen upon comparison between the FTIR Spectra of the reactants and resultant products below, the isocyanatosilane was completely grafted upon the alkyl guanidium polymer backbone under these reaction conditions.

To test the ability of the antimicrobial to kill bacteria in solution, 99 ml of phosphate buffered saline (PBS) in a 250 ml flask was inoculated with $1-3 \times 10^7$ CFU/ml of either *Staphylococcus aureus* ATCC 6538 or *Klebsiella pneumoniae* ATCC 4352. One ml of active at 500 µg/ml in water was added to bring the final concentration of active agent in solution to 5 µg/ml and the flasks were shaken on an orbital shaking platform at 250 rpm. For negative controls, 1 ml of water was added in place of active agent. At 30 s and 5 m, 100 µl aliquots were removed from the flasks and added to 900 µl Dey-Engley neutralizing broth. Serial dilutions were performed and plated onto tripticase soy agar plates. Plates were incubated at 37° C. for 24 h then colonies were counted.

TABLE 1

Solution testing of Polymers 120, 320, and 720

| Active agent | $Log_{10}$ Reduction *S. aureus* | | $Log_{10}$ Reduction *K. pneumoniae* | |
| --- | --- | --- | --- | --- |
| | 0.5 min. | 5 min. | 0.5 min. | 5 min. |
| Negative control | 0 | 0 | 0 | 0 |
| Polymer 120 | 3.1 | >5 | 4.66 | >5 |
| Polymer 720 | 2.62 | >5 | 1.92 | 4.82 |
| Polymer 320 | 1.33 | 2.01 | 4.57 | >5 |

Samples of commercially available single-use dental bibs that consist of plastic-backed paper were acquired. The antimicrobial polymers 120, 320, and 720, were applied to the paper using an airbrush to provide an even coating. Samples were weighed prior to and after application to determine solids coating/cm². Samples were treated with various of amounts of either the unmodified polymer or the glycidol modified polymer.

To assess the leaching of the antimicrobial polymer from textiles, a method is employed that utilizes the property that tetrabromofluorescein (Eosin Y) changes color with exposure to the guanidine moieties of polymers 120, 320, and 720. A square of treated paper bib that was coated with a total of 1000 µg of polymer was placed in 50 ml water and shaken on an orbital shaking platform for 30 minutes. 1 ml of wash water was removed from each jar and 10 ul of 2 mg/ml Eosin Y solution was added to each sample. A color change from orange to pink indicates presence of the polymer in the wash water and thereby denotes leaching. Color change was determined visually and by absorbance at 540 nm using a UV-vis spectrometer. There was no leaching detected from any of polymers 120, 320, or 720, from paper bibs.

For AATCC Test Method 100, $1-5 \times 10^5$ CFU of *K. pneumoniae* ATCC 4352 or *S. aureus* ATCC 6354 in LB Broth were added to treated and untreated 4.8 cm diameter circles of fabric samples. The inoculated samples were placed in a glass jar and incubated for 5 m before 50 ml of DE Neutralizing Broth is added. The jar was vigorously shaken for 1 m and then standard plate counts were performed.

TABLE 2

AATCC 100, 5 minute exposure

| | Active loading (µg/cm²) | $Log_{10}$ Reduction *S. aureus* | $Log_{10}$ Reduction *K. pneumoniae* |
| --- | --- | --- | --- |
| Untreated control | 0 | 0 | 0 |
| Polymer 120 | 27 | >4 | >4 |
| Polymer 120 | 56 | >4 | >4 |
| Polymer 720 | 20 | 1.22 | 1.74 |
| Polymer 720 | 40 | 2.74 | 2.47 |

While the invention is described through the above-described exemplary embodiments, it will be understood by those of ordinary skill in the art that modifications to, and variations of, the illustrated embodiments may be made without departing from the inventive concepts disclosed herein. For example, although some aspects of making and using Applicant's antipathogenic composition has been described, those skilled in the art should readily appreciate that functions, operations, decisions, etc., of all or a portion of each step, or a combination of steps, of the series of steps described may be combined, separated into separate operations or performed in other orders. Moreover, while the embodiments are described in connection with various illustrative structures and functional groups, one skilled in the art will recognize that the antipathogenic composition can be embodied using a variety of related structures and functional groups. Furthermore, disclosed aspects, or portions of these aspects, may be combined in ways not listed above. Accordingly, the invention should not be viewed as being limited to the disclosed embodiment(s).

The present invention may be embodied in other specific forms without departing from its spirit or essential characteristics. The described implementations are to be considered in all respects only as illustrative and not restrictive. The scope of the invention should, therefore, be determined not with reference to the above description, but instead should be determined with reference to the pending claims along with their full scope or equivalents, and all changes which come within the meaning and range of equivalency of the claims are to be embraced within their full scope.

The invention claimed is:

1. An antipathogenic copolymer, comprising a structure:

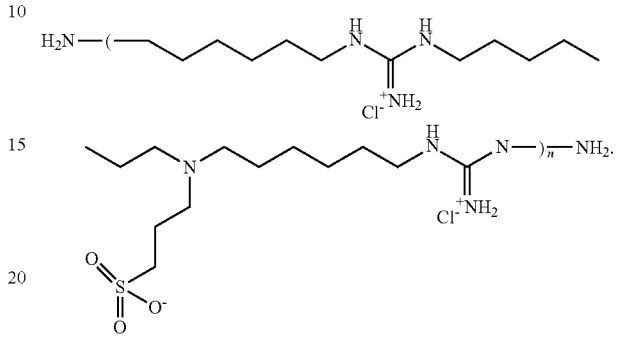

wherein n is between about 10 and about 100.

2. An antipathogenic copolymer, comprising a structure:

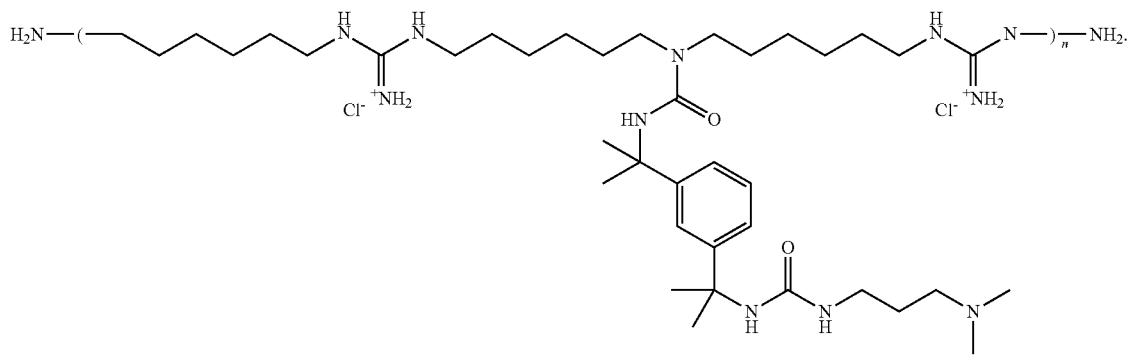

wherein n is between about 10 and about 100.

3. An antipathogenic copolymer, comprising a structure:

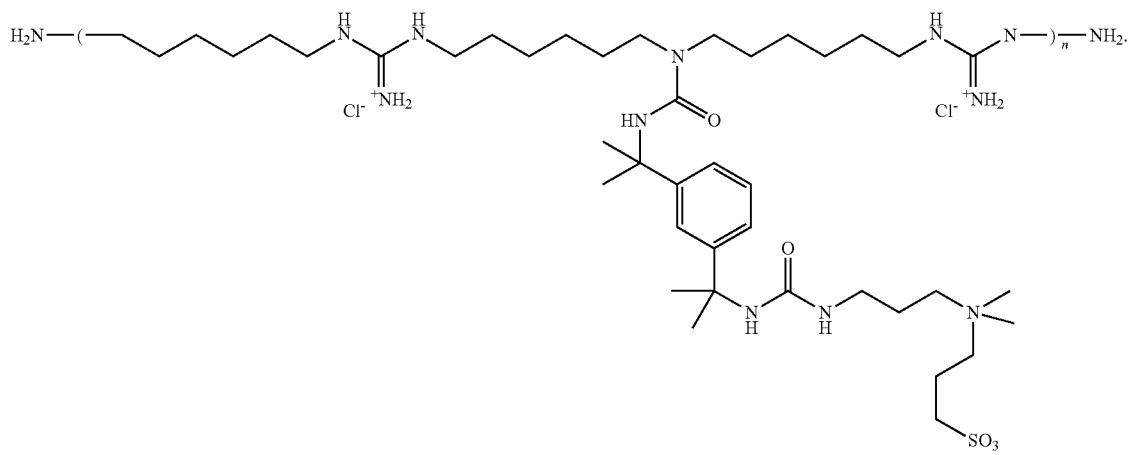

wherein n is between about 10 and about 100.

4. An antipathogenic copolymer, comprising a structure:

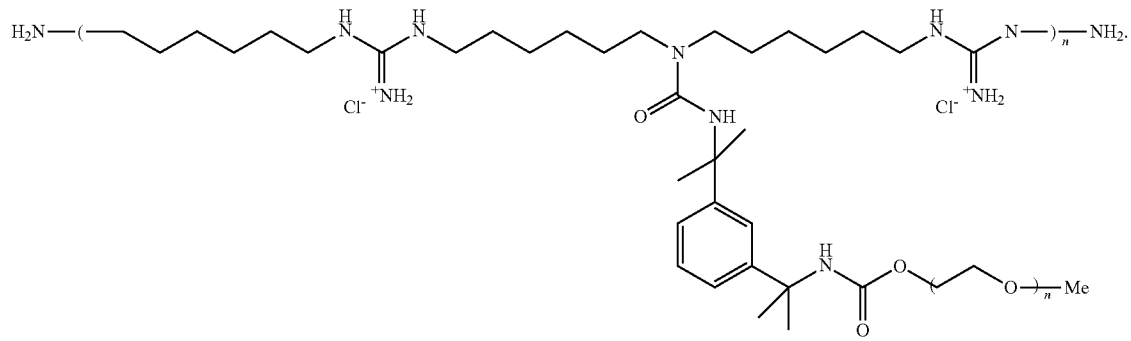

wherein n is between about 10 and about 100.

5. An antipathogenic copolymer, comprising a structure:

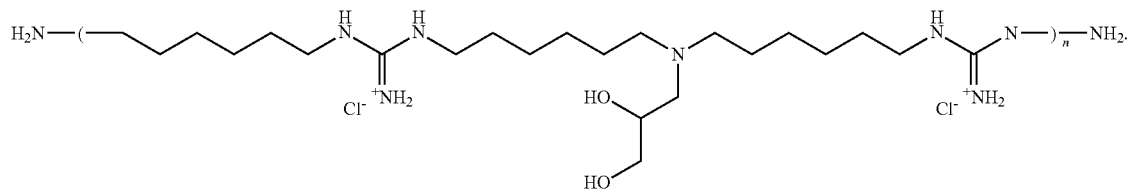

wherein n is between about 10 and about 100.

6. An antipathogenic copolymer, comprising a structure:

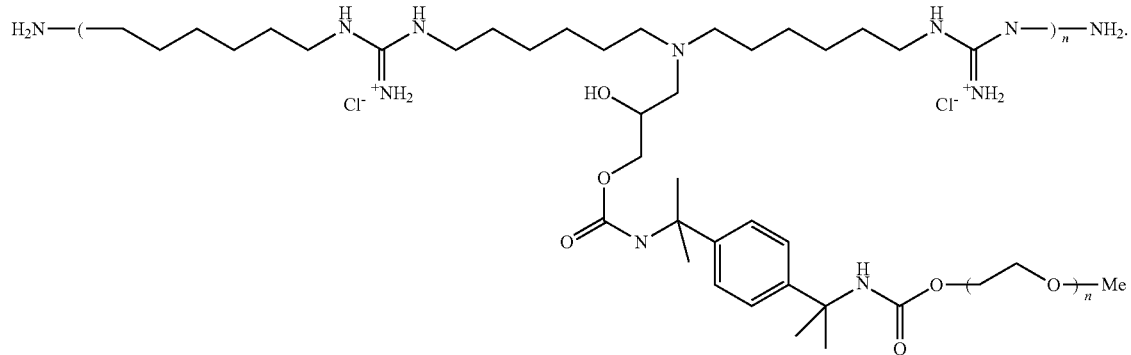

wherein n is between about 10 and about 100.

7. An antipathogenic copolymer, comprising a structure

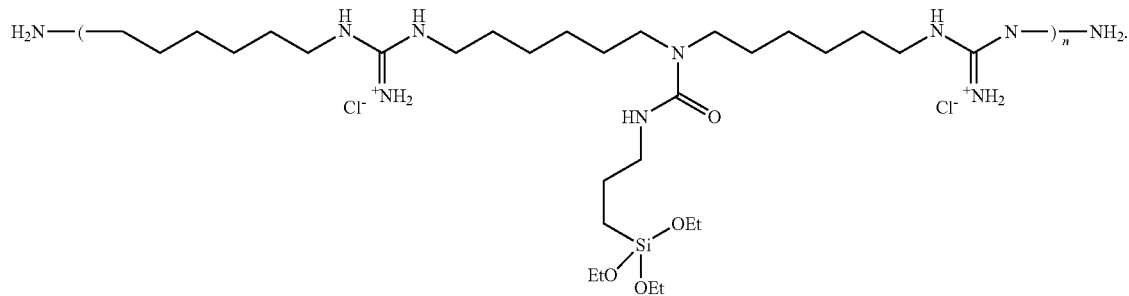

wherein n is between about 10 and about 100.

* * * * *